United States Patent [19]

Berlad et al.

[11] Patent Number: 5,293,195
[45] Date of Patent: Mar. 8, 1994

[54] REDUCTION OF IMAGE ARTIFACTS CAUSED BY COMPTON SCATTER

[75] Inventors: Gideon Berlad; Dov Maor; Yigal Shrem; Adrian Soil, all of Haifa, Israel

[73] Assignee: Elscint Ltd., Haifa, Israel

[21] Appl. No.: 700,420

[22] Filed: May 15, 1991

[30] Foreign Application Priority Data

Jun. 11, 1990 [IL] Israel ..................... 094691

[51] Int. Cl.⁵ ............................. G06F 15/00
[52] U.S. Cl. .......................... 364/413.24; 364/413.23; 250/324
[58] Field of Search ....................... 364/413.24, 413.23; 378/87; 250/324

[56] References Cited

U.S. PATENT DOCUMENTS 4,780,823 10/1988 Stoub et al. ............ 364/413.13
4,839,808 6/1989 Koral et al. ............ 364/413.24

OTHER PUBLICATIONS

B. Axelsson et al., Subtraction of Compton-Scattered Photons in Single-Photon Emission Computerized Tomography, Journal of Nuclear Medicine 25: 490–494, 1984.

*Primary Examiner*—Roy N. Envall, Jr.
*Assistant Examiner*—Khai Tran
*Attorney, Agent, or Firm*—Sandler Greenblum & Bernstein

[57] ABSTRACT

Correction for Compton scattering is effected by analysis of the energy spectra. More particularly, a measured energy spectrum is constructed per location from detected counts that are stored according to their measured energy as well as according to the location of gamma ray infingement on a scintillating detector. The measured spectrum comprises scattered and unscattered photons. A physically correct trial function enables the separation of overlapping contributions of scattered and unscattered photons. The trial function includes multiple collision terms that are preferably constructed using the Nishina-Klein equations describing photon Compton scatter probability distributions. The count of unscattered photons per location is derived from the measured spectrum by locally fitting to the trial function. The count of the unscattered photons per location is used to produce the improved images with reduced artifacts caused by Compton scatter.

44 Claims, 2 Drawing Sheets

REDUCTION OF IMAGE ARTIFACTS CAUSED BY COMPTON SCATTER

FIELD OF THE INVENTION

This invention is concerned with gamma camera imaging and more particularly, with methods and systems for obtaining images with a greatly reduced content of Compton scattered events: i.e., practically Compton free images.

BACKGROUND OF THE INVENTION

In passing through the human body, gamma photons have a certain probability of scattering due to the Compton effect. Such scattering changes the direction of motion of the photons and the energy of the photons. When a photon that has been scattered is recorded in the gamma camera image, false position information is derived from the scattered photons.

In principle, the scattered photons should be discarded. However, it is not easy to arrive at criteria that are efficient and effective for discarding scattered photons. For example, an energy level criterion is not effective because even though the photon loses part of its energy in the scattering process, the energy resolution of a typical gamma camera is such that there is a large amount of overlap in acceptable recorded energy between scattered and unscattered photons.

An object of the present invention is to both qualitatively and quantitatively improve the recorded images by significantly eliminating the contribution of the scattered photons to the final image and obtaining the practically Compton free images within seconds after acquisition. There are many prior art methods that also reduce, or attempt to reduce the contribution that the scattered photons make to the final image. However, of all the prior art methods and systems known, no high quality, practical method is known wherein the contribution of the scattered photons to the final image is significantly reduced and the final image is shown to be qualitatively and quantitatively practically free of Compton scatter contamination.

Some of the prior art methods are:

(a) Dual Window Acquisition

In addition to acquiring data using the standard, full energy window around the peak energy, a second image is acquired at "low" energy. The second image is then multiplied by an empirical constant and subtracted from the first image to reduce the effect of the scattered events on the final image.

(b) The Method of Axelsson et al (see the article "Subtraction of Compton-Scattered Photon Emission Computerized Tomography", J. Nuc. Med. 25, pp. 490-494, 1984)

This is a spatial deconvolution method which is designed to extract the exponential tail caused by Compton scattering from the point spread function. The magnitude of the exponential tail is considered a constant throughout the image.

(c) Weighted Acquisition Module

This method has been described in U.S. Pat. No. 4,780,823. Basically, what is described in the Patent is a constant spatial filter applied on the fly over the whole area of the image. The method does not remove the Compton scattered events at all, but tends to sharpen edges blurred by the scattering.

(d) The Method of Koral et al

This method is taught in U.S. Pat. No. 4,839,808. Therein the energy spectrum is fitted at each given location with a photopeak shaped curve combined with a third order polynomial that is assumed to represent the Compton scatter spectrum. The result of the fit is assumedly a separation of events at each point into a scattered and an unscattered portion. In order to obtain reasonable statistics and also save computation time, the energy spectra are in practice analyzed on a coarse spatial grid. The values of the Compton scatter fraction are then interpolated to obtain values for a finer imaging grid.

The basic shortcoming which all of the above methods have in common is that they do not utilize the innate physical properties of the energy spectrum to account for the Compton scattered events. As a result, the above Compton scatter correction methods all inherently cannot possibly correctly calculate and subtract Compton scattered events.

The methods (a) and (b) described above, are both totally empirical and non-local. As a result, neither method has been successful in overcoming artifacts due to Compton scattering and as a result, in practice, they are not used.

The weighted acquisition module method does not even attempt to separate the Compton scattered events from the unscattered events; rather, the method sharpens somewhat the edges blurred by the scattering. It does have limited use in qualitative images, but is practically totally useless in quantative SPECT imaging, which is expected to be a main application of scatter corrected imaging.

The method of Koral et al suffers from several drawbacks. The main drawback is the fact that the third order polynomial used for fitting the Compton scatter distribution does not truly define the physical distribution of the Compton scatter events. The third order polynomial is unrestricted especially at the high energy Compton scatter thresholds of the spectrum which overlap the photopeak. The high energy portion of the overlap is the most relevant area in which it is difficult to eliminate Compton scatter by conventional methods of energy windows.

With the fit being performed thousands of times per image, it is practically impossible to prevent using many incorrect composite curves which result in erroneous image quantitation and artifacts.

BRIEF DESCRIPTION OF THE PRESENT INVENTION

The present invention is somewhat similar to the system of Koral et al as described in the Patent. The present invention locally analyzes the energy spectrum and attempts to fit it with a "trial" function composed of a photopeak component of known energy shape and unknown magnitude and a Compton scatter component unknown both in shape and in magnitude. However, instead of using an arbitrary polynomial to fit the Compton component energy spectrum as used by Koral et al, the true physical characteristics of the Compton process are used to derive Compton multi-scatter functions which are subsequently used to construct the Compton component energy spectra. The fit, therefore, provides quantitative information on both photopeak and Compton components.

In greater detail, the following "inputs" are used to determine the unknowns; i.e., the magnitude of the photopeak component, the shape and magnitude of the Compton multi-scatter components:

1) The measured energy spectrum per pixel. This includes counts due to scattered and unscattered photons, 2) The system energy spread function. For the isotope center line, this is the photopeak energy shape.

The shape of the Compton component of the trial function is derived using the following steps:

1) The Nishina-Klein equation, describing the physical relativistic scattering of photons and electrons is converted into a probability distribution for a photon to scatter from a given energy to a lower energy in a single interaction.

2) By repeated convolutions, probability distributions for higher order interactions are constructed.

3) A superposition of the various orders with local coefficients of as yet unknown values, is constructed.

4) This superposition is convolved with the system energy spread function to yield the physical Compton multi-scatter component.

By locally fitting this trial function to the measured energy spectrum of acquired data, the values of the multi-scatter Compton coefficients and the photopeak magnitude are obtained. This enables the removal of Compton contamination from the acquired data.

The execution of the local fitting is preferably expedited by orthonormalizing the set of the multi-scatter probabilities. The orthonormalization can be achieved, e.g. by a Graham-Schmitt procedure. In practice, instead of solving for the coefficients of Compton multi-scatter probabilities, the coefficients of the orthonormalized functions are the unknowns which are determined.

An alternative system of the present invention also treats the problem of improving the statistics for the calculations to compensate in a manner more accurate than the manner used by Koral et al. In the alternative system of the present invention. The smoothness of the Compton distribution is utilized in summing the Compton scatter data over a "quasi-local" area; i.e., in a $(2n+1) \times (2m+1)$ rectangle of pixels for the fit, where m and $n = 0.1.2 \ldots$ The value obtained from the rectangle of pixels is divided by the number of pixels in the rectangle and is assigned to the central pixel of the rectangle. This calculation is repeated for each pixel. This "quasi-local" method is more accurate than the interpolation method used by Koral et al. Moreover, computation time is approximately the same in the present method as is computation time required by the Koral et al interpolation method. The actual algorithm that is preferred is one of continuously updated rectangles such that the time of processing is practically independent of the number of pixels in the rectangle.

The actual fit of the "trial" function to the local or quasi-local measured energy spectra can be done using many methods. In a preferred embodiment either a least square fit or a maximum likelihood method is used. The maximum likelihood method is more time consuming than the least square fit method, however it takes explicitly into account the Poisson statistics in gamma ray processes.

In accordance with a preferred aspect of the present invention, a method of eliminating the contribution of Compton scattered photons on an image produced by a gamma ray imaging system is provided, said method comprises the steps of:

detecting as counts photons impinging on a gamma ray detector responsive to gamma radiation from a source.

determining an X,Y coordinate location for each detected count according to the location of the impingement of the photons on the detector.

measuring the energy of the impinging photons, using a plurality of energy windows that together span an energy range with each window extending over a portion of the energy range, placing each detected count in a location in a memory matrix assigned to each of said energy windows according to the measured energy of the impinging photon, said memory matrices each being digital images corresponding to a single energy window comprising X,Y co-ordinates, determining a measured energy spectrum per X,Y location by using the counts accumulated in each of the memory matrices for each X,Y coordinate location, said measured energy spectrum including counts produced by both scattered and unscattered photons, calculating the energy distribution of Compton multi-scattered photons using Compton multi-scattered components, where "multi-scattered" includes at least first order scatterings, convolving the calculated energy distributions of the multi-scattered photons with a spread function typical of a gamma ray imaging system to obtain system dependent energy distribution of the Compton multi-scattered photons, constructing a trial function by:
summing the system dependent energy distributions of the Compton multi-scattered photons with unknown coefficients, one for each order of scattering, and adding the contribution of unscattered photons as a coefficient times the photopeak energy shape, fitting the constructed trial function to the measured energy spectrum per X,Y coordinate location to solve the unknown X,Y coefficients and thus determine the counts per X,Y location of the unscattered photons, and using the counts of unscattered photons per pixel to provide a Compton free image.

According to a feature of the present invention, calculating the energy distribution of scattered photons includes converting the Nishina-Klein equation to a first order probability distribution to determine the energy distribution of first order scattered photons, and convolving the first order probability distribution to obtain higher order scattered photon distributions where such higher order scattered photon distributions are being considered.

In accordance with an added feature of the present invention, a set of discrete functions is obtained from the energy distribution by averaging or integrating the energy distributions for each of the energy windows.

Yet another added feature of the present invention is the conversion of the discrete functions into an orthonormal set of functions to decrease the number of calculations.

In accordance with yet another added feature of the present invention, obtaining the discrete functions for the energy spectrum of the scattered photons is accomplished quasi-locally using "large" pixels. This use of "large" pixels for the comparatively smooth Compton distributions compensates for the low statistical counts in each of the regular pixels.

In accordance with yet another feature of the present invention. The fitting is accomplished using least square fitting computations. Alternatively, maximum likelihood solutions are used.

Another feature of the present invention is that the derivations of all energy shapes used in the trial function are data independent. Therefore, such shapes can either be stored or calculated prior to the data processing that generates Compton free images.

BRIEF DESCRIPTION OF THE DRAWINGS

The above mentioned objects and features of the present invention along with additional objects and features will be best understood when considered in the light of the following description made in conjunction with the accompanying drawings; wherein.

GENERAL DESCRIPTION

Figure 1:
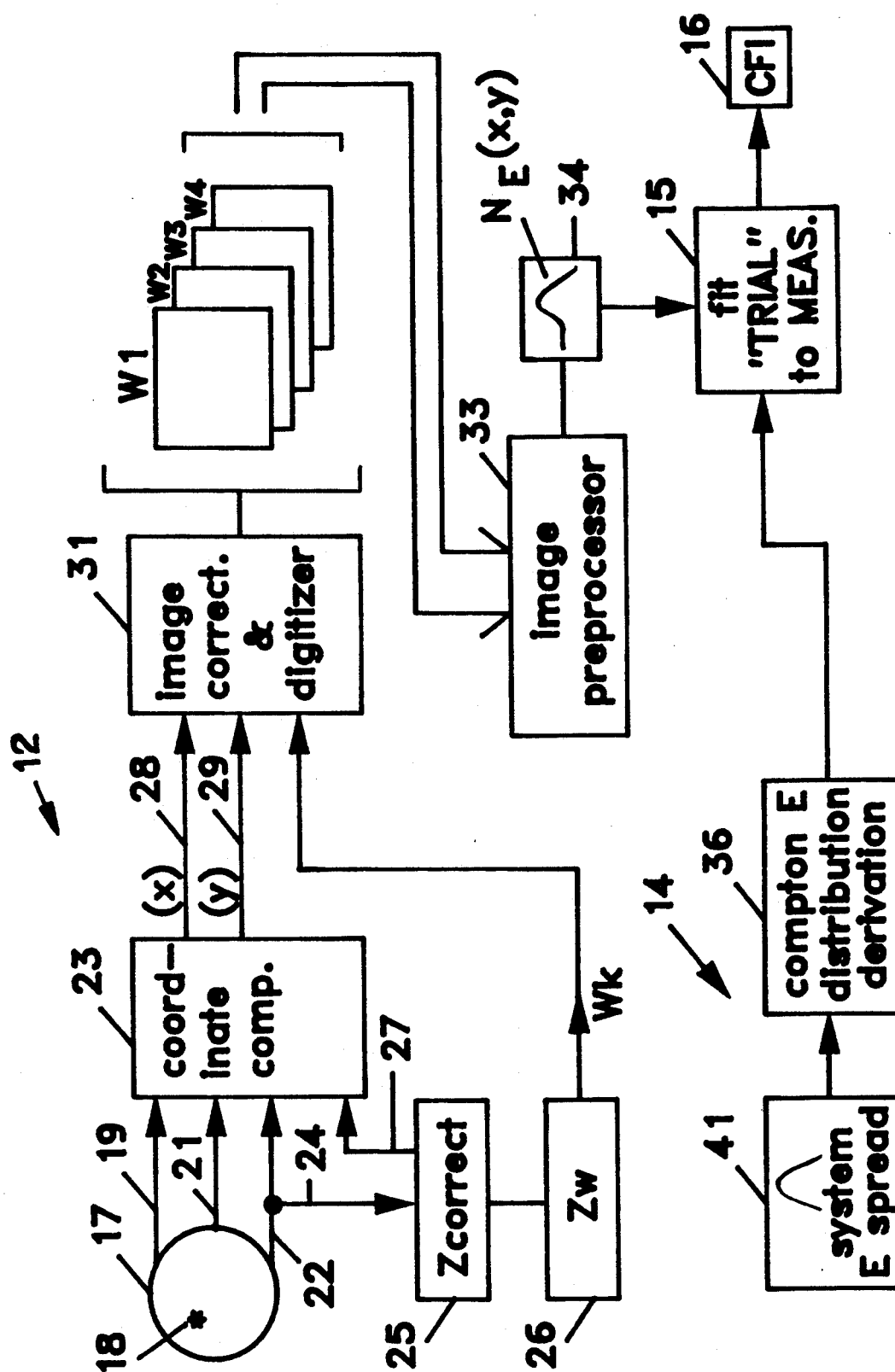
FIG. 1 is a block diagram showing of a gamma radiation imaging system for providing Compton free images.

FIG. 1 at 11 shows in block diagram form the inventive gama camera system for producing Compton free images. FIG. 1 comprises a measured energy spectrum stage 12, a trial function preparation stage 14 and a curve fitting or computation stage 15 which provides the Compton free image 16.

The measured energy spectrum stage 12 comprises a gamma radiation detector 17. The gamma radiation detector 17 provides electrical signals responsive to photons impinging on the face thereof such as is indicated at 18. When a photon impinges on the face of the detector, electrical signals are provided on conductors 19, 21 and 22. These conductors 19, 21 and 22 are directed immediately to a coordinate computer 23 which determines the X and Y location of the impingement of the photon 18 on the detector 17.

The conductors 22 and 24 carries an electrical representation of the energy of the photon. The electrical representation of the energy is provided to an energy (Z) correction circuit 25. An energy processing circuit 26 divides the range of the energy detected into a number of energy windows predetermined by the system operator.

When the energy is within certain limits the energy correction circuit sends an enable signal over conductor 27 which enables the coordinate computer to determine the X and Y locations. This information is directed to an image corrector and digitizer circuit 31. The image corrector and digitizer circuit 31 corrects and digitizes the X,Y coordinates of each event. The information on the number of events is placed into a plurality of matrices 32 depending on the photon's energy. Each of the matrices is a memory that retains the count of events per X,Y location for a particular energy window such, as for example, a window that extends from 22 kev to 25 kev, for window #1 and 25 kev to 28 kev for window #2, etc. The windows are shown as W1, W2, W3 extending to Wn where n is the predetermined number of energy windows.

The matrices are thus divided into X,Y locations that correspond to the location of the event on the detector.

The X,Y locations also correspond to pixels in the final image. An imaging preprocessor 33 receives the data pixel by pixel from each of the windows and computes measured or acquired energy spectrum N- per pixel as shown at block 34. This acquired energy spectrum includes both the counts of unscattered photons and scattered photons.

The trial function stage 14 of FIG. 1 prepares a theoretical or trial energy distribution n(X,Y,E) including scattered and unscattered events. Herein:

$$n(X,Y,E) = N_P(X,Y) \cdot P(\epsilon_0,\epsilon) + \sum_m Q_m(X,Y) \int d\epsilon' P(\epsilon',\epsilon) \pi(\epsilon_0,\epsilon) \quad (1)$$

where:
- $\epsilon = E/m\text{-}C^2$, the photon energy in units of electron rest energy, $m\text{-}C^2$,
- $P(\epsilon',\epsilon) = $ a typical energy spread function at energy $\epsilon'$ for the system. Its shape has been measured and is known,
- $\pi_m(\epsilon_0,\epsilon) = $ the energy distribution of events caused by photons scattered m-times from original energy $\epsilon_0$ to energy $\epsilon'$ (i.e. the shape of the energy probability distribution of the m-times scattered photons),
- $N_P(x,y) = $ the spatial distribution (counts/pixel) of the events caused by unscattered photons,
- $Q_m(x,y) = $ the spatial distribution (count/pixel) of the events caused by photons scattered m-times,
- $\epsilon_0 = $ the original energy of the photon,
- $\epsilon = $ the measured energy of the photon, and
- $\epsilon' = $ an intermediate energy of a photon.

An important purpose of the invention is to determine $N_P(x,y)$, the spatial distribution of unscattered events.

To determine the count of events per pixel, block 15 fits the computed values of the trial distribution $n(x,y,\epsilon)$ to the measured values NE(x,y). The output of the fit provides the unscattered spatial distribution $N_P(x,y)$. With the knowledge of the unscattered spatial distribution the Compton free image is produced as indicated at 16.

Figure 2:
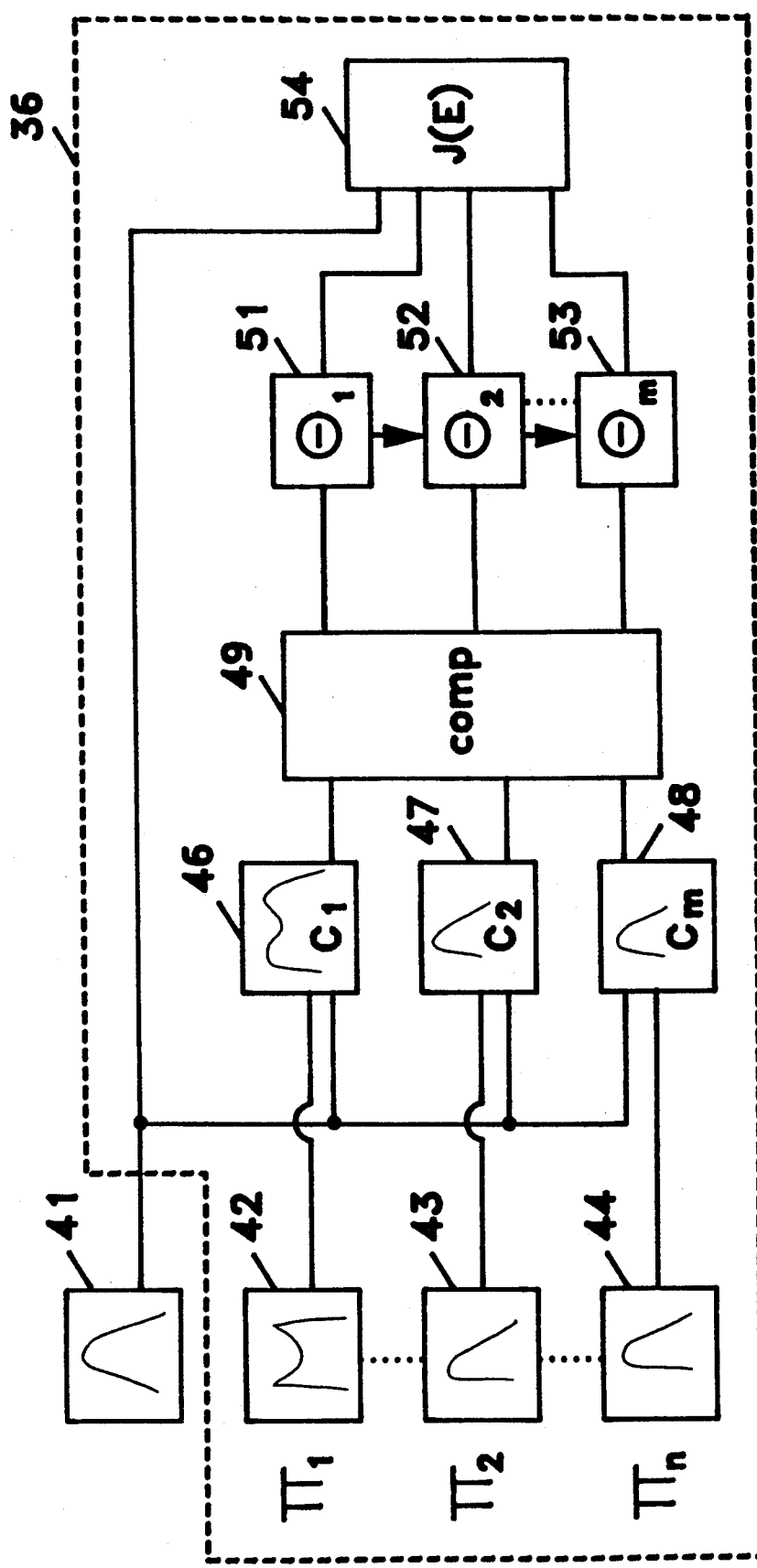
FIG. 2 represents details of preparations, computations and operations used in the system shown in FIG. 1.

Details of the computations that occur in the trial function preparation section 14 of FIG. 1 are indicated in FIG. 2. More particularly, as shown in FIG. 2 values based on the system energy spread function shown in block 41 of FIG. 1 and FIG. 2 are entered into block 36 of FIGS. 1 and 2. The energy spread function of the system is assumed to be known. It is measured once for the system or a typical system spread function is used and is kept in the memory of the system. The measurement is easily accomplished by providing sources of gamma radiation of known energy and detecting the radiation with the equipment 11 of FIG. 1, for example. The detection is made without any Compton scatter media between the energy source and the detector. This provides the energy spread function for a monoenergetic source due to the detector energy resolution such as shown at block 41.

The preparation block 36 computes $\pi_m$; that is, the energy distribution of the scattered photons for each scattering order.

This is done by using the Nashina-Klein equation to derive the different orders of scattered unpolarized photons: i.e.:

$$\pi_1(\epsilon_o, \epsilon_1) = \begin{cases} \frac{1}{\epsilon_o^2}\left[\frac{\epsilon}{\epsilon_o} + \frac{\epsilon_o}{\epsilon} - \left(\frac{1}{\epsilon} - \frac{1}{\epsilon_o}\right)\left(2 - \frac{1}{\epsilon} + \frac{1}{\epsilon_o}\right)\right]; \frac{\epsilon_o}{1+2\epsilon_o} \leq \epsilon \leq \epsilon_o \\ 0 \quad : \text{elsewhere} \end{cases} \quad (2)$$

The higher orders of scatters are derived by repeated convolutions using the equation:

$$\pi_m(\epsilon_o,\epsilon_m) \begin{cases} \int_{\epsilon_m}^{\epsilon_o} d\epsilon_{m-1}\pi_{m-1}(\epsilon_o,\epsilon_{m-1})^*\pi_1(\epsilon_{m-1},\epsilon_m); \frac{\epsilon_o}{1+2m\epsilon_o} \leq \epsilon \leq \epsilon_o \\ 0 \quad : \text{elsewhere} \end{cases} \quad (3)$$

Note that the equations are solved recursively in that each higher order equation requires knowledge of the lower orders.

The energy distribution of the Compton scatter photons provides a curve independent of the system for each order of scatter. However, this system independent curve is acted upon by the system energy spread function to provide the system dependent Compton multi-scattered energy distributions denoted by $C_m(\epsilon_o,\epsilon)$. The shapes of the $C_m(\epsilon_o,\epsilon)$ distributions are obtained by convolving $\pi_m$ with the system energy spread function $P(\epsilon',\epsilon)$:; i.e.:

$$C_m(\epsilon_o,\epsilon) = \int d\epsilon' \pi_m(\epsilon_o,\epsilon') P(\epsilon',\epsilon) \quad (4)$$

This set of equations provides the shape of the Compton energy distributions for each order of scatter after being operated on by the system energy spread function. FIG. 2 indicates the computations resulting in the $\pi_m$ values using the Nishina-Klein equation in box 42, 43 and 44 for $\pi_1$ and consequently $\pi_2, \ldots \pi_m$.

The shapes of $\pi_1$, $\pi_2$ and $\pi_m$ in blocks 42, 43 and 44 are shown as being convolved with the system energy spread function of block 41 in blocks 46, 47 and 48 respectively, thereby providing the shapes C1, C2, etc. The computations to determine $\pi_1$, $\pi_2$, etc., and C1, C2, etc. are indicated as being recursive by the dotted line arrows going from $\pi_1$ to $\pi_2$, etc., and from C1 to C2, etc.

A method for drastically reducing the number of computations is provided by this invention. This reduction in computation is accomplished by orthonormalization of the set $C_m(\epsilon_o,\epsilon)$. The orthonormalization is provided by constructing an orthonormal function (vector) set $\theta_m$ using the Graham-Shmidt procedure:

$$\theta_1 = C_1/\sqrt{<C_1^2>} \quad (5)$$

$$\theta_2 = (C_2 <\theta_1 \cdot C_2> \theta_1/\sqrt{<C_2^2> - <\theta_1 \cdot C_2>^2}$$

$$\theta_m = \left(C_m - \sum_{l=1}^{m-1} <\theta_l \cdot C_m>\theta_l\right) /$$

$$\sqrt{<C_m^2> - \sum_{l=1}^{m-1} <\theta_l \cdot C_m>^2}$$

Where sums (integrals) over energy are defined by:

$$\sum_E F<C_1>(E) = <F>$$

Note that the array set $\{\theta_m\}$ obeys:

$$<\theta_i,\theta_j> = \delta_{i,j}\begin{cases} 1, i = j \\ 0, i \neq j \end{cases}$$

The orthonormalization is accomplished in computer 49 and the results: i.e., $\theta_1, \theta_2 \ldots \theta_m$ are shown in blocks 51, 52, 53, for example.

The Compton sum (EQ(4)) can be rewritten using the $\theta_k$'s:

$$\sum_m Q_m C_m = \sum_m Q_m \sum_k <C_m \cdot \theta_k> \cdot \theta_k \quad (*) \quad (6)$$

$$= \sum_k \left(\sum_m <C_m \cdot \theta_k> Q_m\right) \cdot \theta_k$$

$$= \sum_k q_k \cdot \theta_k$$

where:

$$q_k = \sum_m <C_m \cdot \theta_k> \cdot Q_m$$

*[with an orthonormal base $\{\theta_m\}$ any vector $v$ can be represented as a superposition of an array of $\theta_m$':

$$v = \sum_m <v \cdot \theta_m> \theta_m] \quad (7)$$

The trial distribution now reads:

$$n(X,Y;E) = Np(X,Y) P(E_o,E) + C(X,Y;E_o,E) \quad (8)$$

where:

$$C(X,Y;E_o,E) = \sum_k q_k(X,Y)\theta_k(E_o,E) \quad (9)$$

Hereafter the known energy spread function, P is normalized such that $<P>=1$.

In a preferred implementation, a least square fit is used. More particularly, with the trial function n(X,Y;E) of equation (1) and the multi-window acquisition results $N_E(X,Y)$ from block 34, a solution is sought for the number of counts caused by unscattered photons $N_P(X,Y)$ that will minimize the sum of the squares of differences for each pixel $\delta(X,Y)$:

$$\delta(X,Y) = <[n(X,Y;E) - N_E(X,Y)]^2> \qquad (10)$$

More particularly, in the block 15 the following "fit" operation is performed, i.e., $$\frac{\partial \delta}{N_P} = 0, \text{ and} \qquad (11)$$

$$\frac{\partial \delta}{q_k} = 0, \text{ where } k = 1,2,\ldots \qquad (12)$$

It can be shown that the solution of these equations is:

$$N_P(X,Y) = <N_E(X,Y) \cdot J(E)> \qquad (13)$$

$$q_k(X,Y) = <N_E(X,Y) \cdot G_k(E)> \qquad (14)$$

where:

$$J(E) = \frac{P(E_o,E) - \sum_k <P \theta_k> \cdot \theta_k(E_o,E)}{<P^2> - \sum_k <P \cdot \theta_k>^2} \qquad (15)$$

$$G_k(E) = \theta_k(E_o,E) - <P \theta_k> \cdot J_{<E>} \qquad (16)$$

Note that since J(E) and $G_k(E)$ are data independent, they can be apriori derived as indicated in FIG. 2 by block 54 which shows computing J(E) using $\theta_1, \theta_2 \ldots \theta_k$ and P. The "per-pixel" operations entail only the evaluation of the scalar product $$N_P = <N_E \cdot J(E)>. \qquad (17)$$

The fit, therefore, determines the per pixel Compton scatter free count $N_P$.

To compensate for low statistics per pixel per energy window, the relative constancy of scatter distributions over large spatial domains is put to advantage by use of a "quasi-local" solution. More particularly, an expanded or "large" pixel is used. Thus, if the top pixel is $(X_o, Y_o)$ the spatial window W is defined as:

$$X_o - W \leq X \leq X_o + W, Y_o - W \leq Y \leq Y_o + W \qquad (18)$$

of area $s = (2W+1)^2$.

When the Compton component of the entire window s, $C^s$ is computed, the "per-pixel" Compton activity, $C^1$ can be approximated by its average:

$$C^1 = C^s/S. \qquad (19)$$

The measured activity in the spatial window s (symmetric around the coordinates (X,Y)) is denoted as $N_E^s(X,Y)$, and the (X,Y)-pixel activity is denoted as $N_E^1(X,Y)$. A single parameter fit is done to find the local photopeak count. It can be shown that this is given by:

$$N_P^1(X,Y) = <N_E^1(X,Y) \cdot A_E^1 + N_E^s(X,Y) \cdot A_E^s> \qquad (20)$$

where:

$$A_E^1 = P(E)/<P^2> \qquad (21)$$

$$A_E^s = [J(E) - A_E^1]/s \qquad (22)$$

Solving for $N^1_P(X,Y)$ gives the count/pixel of the Compton free image.

An alternative fitting method is the Maximum Likelihood Method. Given the measured activities $\{N_E\}$ the joint Poisson probability with respect to the parameters of the trial function n(E) are maximized; i.e., find n(E) such that $$P = \pi_E \left( \frac{n(E)^{N_E}}{N_E!} e^{-n(E)} \right) = \text{maximum} \qquad (23)$$

or, since P is positive:

$$\ln P = <N_E \ln n(E) - n(E) - \ln N_E!> = \text{maximum} \qquad (24)$$

It can be shown that for the maximum likelihood solution:

$$<n(E)> = <N_E>$$

which enables eliminating $N_P$ from the n(E) function. (Hereafter (X,Y) are implicit, e.g., n(X,Y;E)=n(E). Thus from equations (8) and (9) it follows that:

$$n(E) = <N_E> \cdot P + \sum_k q_k(\theta_k - <\theta_k> \cdot P) \qquad (25)$$

Calculating the derivatives of lnP with respect to $q_k$ and setting the resulting equation to 0 as required by the maximum condition, the following equations are obtained:

$$<\frac{N_E}{n(E)} (\theta_k - <\theta_k> \cdot P)> = 0; \quad k = 1,2,\ldots \qquad (26)$$

This is a set of non-linear coupled equations and cannot be solved in closed form. Using the multi-gradient method, an iterative solution for the $q_k$s can be obtained. Denoting $\delta q_k$ as the difference between $q_k$ before and $q'_k$ after the iteration $$\delta q_k = q'_k - q_k. \qquad (27)$$

The coupled set of equations is linearized and soluble $$\sum_j M_{ij} \delta q_j = U_i \qquad (28)$$

$$M_{ij} = <\frac{N_E}{n^2(E)} (\theta_i - <\theta_i>P)(\theta_j - <\theta_j>P)> \qquad (29)$$

$$U_i = <\frac{N_E}{n(E)} (\theta_i - <\theta_i> \cdot P)> \qquad (30)$$

After proper convergence of the solution for the array $q_k$ has been attained, the Compton free activity $N_P$ can be obtained from:

$$N_P = <N_E> - \sum_k q_k <\theta_k> \quad (31)$$

Yet another alternative fit is the partial Maximum Likelihood Solution. Suppose that the least square solution provides the approximate functional structure of the Compton component. However, it is desired to introduce the Poisson statistics by changing the ratio of the photopeak to Compton events fraction in order to optimize the joint distribution. The trial function, n(E), then is $$n(E) = <N_E>[f_P \cdot P + (1 - f_P)\hat{C}] \quad (32)$$

where:

$$f_P = \frac{N_P}{<N_E>} \text{ is the photopeak fraction} \quad (33)$$

and $\hat{C}$ is the least square Compton solution, normalized to 1; i.e.:

$$\hat{C} = C/<C> \quad (34)$$

Now, the Maximum Likelihood Equation is maximized with respect to a single parameter, the photopeak fraction, $f_P$. Once $f_P$ is calculated, the scatter-free event distribution $N_P$ can be found using the equation:

$$N_P = f_P <N_E> \quad (35)$$

The optimization equation resulting from the differentiation with respect to $f_P$ reads:

$$< \frac{N_E(P - \hat{C})}{\hat{C} + f_P(P - \hat{C})} > = 0 \quad (36)$$

It is soluble by an iterative Newton-Raphson method:

$$f_P = f_P + \frac{<N_E \cdot \tau>}{<N_E \cdot \tau^2>} \quad (37)$$

where:

$$\tau = \frac{P - \hat{C}}{\hat{C} + f_P(P - \hat{C})} \quad (38)$$

Yet another related method of obtaining the value of $N_P$ involves the semi-local Maximum Likelihood Fit Solution. As for the quasi-local solution, this is implemented here as follows: First a solution is obtained for the square called S surrounding the pixel $X_o, Y_o$, i.e.:

$$S = X_o - W \leq X \leq X_o + W, Y_o - W \leq Y \leq Y_o + W = (2W+1)^2 \quad (39)$$

Once the Compton free component of the entire window has been obtained, either by the full or by the partial Maximum Likelihood method: i.e., $N_P^s(X,Y)$ is known, the slow Compton spatial variance is used by assuming:

$$C^1 = C^s/s \quad (40)$$

to obtain the (X,Y)-pixel Compton free activity:

$$N_P^1 = \frac{N_P}{s} + <N_E^1 - \frac{N_E^s}{s}> \quad (41)$$

In operation, the inventive system locally analyzes the energy spectrum and fits it with a trial function comprising a combination of the unscattered photopeak function and a function representing the Compton scattered spectrum. The function representing the Compton scattered spectrum is derived using the Nishina-Klein formula. The Compton scatter spectrum shape, therefore, inherently reflects the true relativistic distributions of the Compton scatter, unlike the previously used arbitrary polynomials. The Nishina-Klein formula is recursively used to generate the multi-scattered Compton distribution $\pi_m$. Then each $\pi_m$ is convolved with the system energy spread function to obtain $C_m$, the system dependent Compton scatter distributions. The convolved functions are averaged or integrated for discrete windows to obtain discrete arrays required for the calculations. The set of discrete functions $C_1$ is then preferably orthonormalized to reduce the number of computations necessary and assure that the inventive system can provide practically Compton free images within seconds after acquisition. The coefficients of the orthonormalized functions are parameters that provide the scattered counts per pixel. The parameters are determined by fitting the final function comprised of the photopeak component and the scatter component to the measured energy distribution which includes both the scattered and unscattered photons. The local (and quasi-local) fitting optimizes the coefficients of the fit functions.

A unique approach of the invention is that the parameters to be determined are coefficients of the physical Compton scatter functions. The said functions have the correct high energy threshold behavior ensuring correct fit at every point.

The inventive method also preferably improves the statistics for the calculations for the Compton fit by a method that takes advantage of the smoothness of the Compton distribution (quasi-local method). That is, the data in a preferred embodiment is summed over a (2n+1) square pixels for the fit where n is an integer. The values are then attributed only to the central pixel of the square. Similar calculations are done for each pixel.

Preferably a least square fit is used to solve the unknown coefficients, i.e., the amount per pixel of the unscattered events (and if desired for the amount per pixel of the scattered events). However, several variations employing the maximum likelihood fit are also described.

While the invention has been described with regard to specific embodiments, it should be understood that the description is made by way of example only and not as a limitation of the scope of the invention which is defined by the accompanying claims.

What is claimed is:

1. A method of reducing the contribution of Compton scattered photons on an image produced by a gamma ray imaging system, said method comprising the steps of:

detecting as counts photons impinging on a gamma ray detector reponsive to gamma radiation from a source, determining an X,Y coordinate location for each detected count according to the location of the impingement of the photons on the detector using a plurality of energy windows that together span an energy range to obtain the energy of the impinging photons, placing each detected count in an energy compartment of one of a plurality of memory matrices said energy compartment corresponding to one of said plurality of energy windows according to a measured energy of the impinging photons, said plurality of memory matrices each located at X,Y coordinates, said matrices each being digital images, said X,Y coordinates corresponding to the location of the impingement of the photons on the detector and of a pixel in the images, providing a measured energy spectrum per X,Y location using the counts accumulated in each compartment of the matrices at each of the X,Y coordinate locations, said measured energy spectrum including counts produced by both scattered and unscattered photons, calculating the energy distribution of one or more orders of Compton scattered photons using physical relativistic Compton characteristics, convolving the calculated energy distributions of one or more orders of Compton scattered photons with a system energy spread function to obtain a system dependant energy distribution of the one or more orders of Compton scattered photons, constructing a trial function by:

summing the convolved system dependant energy distribution of one or more orders of Compton scattered photons with unknown amplitude coefficients and the contribution of the system spread function with the unknown amplitude coefficients, locally fitting the trial function to the measured energy spectrum to solve for the unknown amplitude coefficients and thus determining the counts of the unscattered photons, and using the counts of the unscattered photons per pixel to provide an image with reduced artifacts due to Compton Scatter.

2. The method of claim 1 wherein said step of calculating the energy distribution of one or more orders of Compton scattered photons using the physical relativistic Compton characteristics comprises using the Nishina-Klein equation for the physical relativistic Compton characteristics wherein the step of calculating the energy distribution of scattered photons comprises the steps of:

converting the Nishina-Klein equation to a first order photon scatter probability distribution to determine the energy distribution of first order scattered photons, and convolving the energy distribution of the first order scattered photons to obtain probability distributions of higher order scattered photons where said distributions of higher ordered scattered photons are used.

3. The method of claim 2 including the step of obtaining a set of discrete functions from the energy distribution of the Compton multi-scattered photons by averaging the calculated Compton energy distributions for each of the energy windows.

4. The method of claim 3 including the step of reducing the number of calculations.

5. The method of claim 4 wherein the step of reducing the number of calculations comprises converting the discrete functions into an orthonormal set of functions.

6. The method of claim 5 wherein the fitting step includes:

using quasi-local pixels to obtain local counts of the scattered photons, and doing a single parameter fit to determine the local photopeak count.

7. The method of claim 6 wherein the step of using quasi-local pixels comprises:

using large pixels comprising a $(2n+1) \times (2m+1)$ rectangle of pixels where both n and m are positive integers and the value of the large pixel is divided by the number of pixels in the large pixel and attributed to the center pixel, and evaluating all pixels in this manner.

8. The method of claim 1 wherein the step of fitting the trail function to the measured energy spectrum is accomplished using least square fitting.

9. The method of claim 1 wherein the step of fitting the trial function to the measured energy spectrum is accomplished using a maximum likelihood fitting.

10. The method of claim 1 wherein the step of fitting the trial function to the measured energy spectrum is accomplished using a partial maximum likelihood fitting.

11. The method of claim 1 wherein the step of fitting the trial function to the measured energy spectrum is accomplished using a combination of said least square fitting and said maximum likelihood fitting.

12. A method of producing practically Compton free images of a patient with a gamma ray imaging system, said method comprising the steps of:

determining a trial function, said step of determining a trial function comprising the steps of:

multiplying a known system energy spread function by an unknown count number due to unscattered photons, convolving at least one order of energy distribution of the scattered photons derived from the probability the physical interaction of the photons, as determined by physical relativistic Compton characteristics of the scattered photons and the known system energy spread function to provide a system dependant set of Compton fit functions, multiplying the system dependant Compton fit functions by unknown numbers corresponding to counts of scatteres photons, measuring locally an energy spectrum of the patient that includes total counts due to scattered and to unscattered photons, locally fitting the trial function to the measured energy spectrum to determine the unknown count number due to unscattered photons, and using the count number due to the unscattered photons to provide the practically Compton free images.

13. The method of claim 12 including determining the unknown count number due to the unscattered photons within seconds of finishing the step of locally measuring the energy spectrum.

14. The method of claim 12 wherein the step of determining the trial energy function includes converting Nishina-Klein's equation to a first order photon scatter probability energy distribution, and using the converted Nishina-Klein equation to obtain the energy distribution of first order scattered photons.

15. The method of claim 14 including the step of convolving the energy distributions of first order scattered photons to obtain energy distributions of higher orders of scattered photons where such higher orders are being considered.

16. The method of claim 15 including the step of obtaining a set of discrete functions from the calculated Compton energy distribution by integrating the Compton energy distribution for each of matrices.

17. The method of claim 16 wherein the step of measuring the energy function includes the steps of:
   determining an X,Y location and an energy of photons impinging on a system photon detector,
   using a plurality of matrices having X,Y pixels corresponding to the impinging locations to accumulate counts of impinging photons, each of said matrices corresponding to one of a plurality of energy windows, said plurality of energy windows spanning an energy range, and
   constructing the measured energy spectrum from the accumulated counts in the matrices.

18. The method of claim 17 including the step of orthonormalizing the discrete functions.

19. The method of claim 18 including using a Graham-Schmitt procedure for the orthonormalization.

20. The method of claim 12 wherein the step of fitting the trial function to the measured energy spectrum includes using a least square fitting.

21. The method of claim 12 wherein the step of fitting the trial function to the measured energy spectrum includes using a maximum likelihood fitting.

22. The method of claim 12 wherein the step of fitting includes using a combination of said least square and said maximum likelihood fitting.

23. A system for reducing the contribution of Compton scattered photons on an image produced by a gamma ray imaging system, said system comprising:
   means for detecting as counts photons impinging on a gamma ray detector at X,Y locations of impingement responsive to gamma radiation from a source,
   means for determining an X,Y location for each detected count according to the location of impingement on the detector.
   means for measuring the energy of the impinging photons,
   a plurality of memory matrices comprised of energy windows that together span an energy range, each of said windows of said matrices extending over a portion of said energy range,
   means for inserting each detected count in a window of a memory matrix of said plurality of memory matrices according to the measured energy of the impinging photon, said matrices each located at spatial X,Y coordinates, said detected counts being inserted at the X,Y coordinate location according to the location of the impingement on the detector,
   said memory matrices accumulating counts at each of the X,Y coordinate locations.
   means for constructing a measured energy spectrum at each X,Y coordinate location using the accumulated counts per window of said matrix per location, said measured energy spectrum including counts produced by scattered and unscattered photons,
   means for obtaining the counts per X,Y locations produced by only the unscattered photons,
   said means for obtaining the counts per X,Y locations produced by only unscattered photons including:
   means for calculating energy distributions of one or more orders of Compton scattered photons using physical relativisic Compton characteristics,
   means for convolving the energy distribution of the one or more orders of Compton scattered photons with the energy spread function of the system to obtain system dependant Compton energy distributions,
   means for constructing a trial function comprising the system energy spread function multiplied by an unknown coefficient of the unscattered photons plus unknown coefficients of the scattered photons multiplied by the system dependant Compton energy distribution,
   means for locally fitting the trial function to the measured energy spectrum to obtain the count of the unscattered photons by solving for the unknown coefficient of the unscattered photons, and
   means for using the count of the unscattered photon to produce a practically Compton free image.

24. A gamma ray imaging system that reduces the contribution of scattered Compton photons on produced images, said system comprising:
   means for detecting as count photons impinging at X,Y coordinate locations in a gamma ray detector responsive to gamma radiation from a source,
   means for determining an X,Y coordinate location per each detected count according to the location of the impingement of the photons on the detector,
   means for measuring the energy of the impinging photons,
   a plurality of memory matrices each having compartments corresponding to a plurality of energy windows, said plurality of energy windows spanning an energy range,
   means for placing each detected count in one of the plurality of compartments according to the measured energy of the impinging photon, said memory matrices each located at X,Y coordinates, said matrices each being digital images and said X,Y coordinates corresponding to the location of the impingement of the photon on the detector and to a pixel in the images,
   means for providing a measured energy spectrum per X,Y location using the counts accumulated in each of the X,Y coordinate locations of the matrices, said measured energy spectrum including counts produced by both scattered and unscattered photons.
   means for calculating an energy distribution of Compton multi-scatter components using physical relativistic Compton characteristics, where multi-scatter includes at least first order scatterings,
   means for convolving the calculated energy distributions of the Compton multi-scatter photons with the system energy spread function to obtain a system dependant energy distribution of the multi-scatter photons with unknown local coefficients,
   means for constructing a trial function including:
   means for summing the convolved multi-scatter photon energy distribution with unknown local coefficients for the at least first order scatterings and the contribution of the system energy spread function with unknown local coefficients,
   means for locally fitting the trial function to the measured energy spectrum to solve for the unknown local coefficients and thus determining the counts per location of the unscattered photons, and means for using the counts of the unscattered photons per pixel to provide a Compton free image.

25. The system of claim 24 wherein said means for calculating the energy distribution of scattered photons comprises:
means for using a Nishina-Klein equation converted to a first order photon scatter probability distribution to determine the energy distribution of first order scattered photons, and
means for convolving the energy distribution of the first order scattered photons to obtain probability distributions of higher order scattered photons where said distributions of higher order scattered photons are used.

26. The system of claim 25 including means for obtaining a set of discrete functions from the energy distribution of the Compton multi-scattered photons by averaging the calculated Compton energy distributions for each of the energy windows.

27. The system of claim 26 including means for reducing the number of calculations.

28. The system of claim 27 wherein the means for reducing the number of calculations comprises means for converting the discrete functions into an orthonormal set of functions.

29. The system of claim 27 wherein the means for fitting includes quasi-local pixels to obtain local counts of the scattered photons and means for doing a single parameter fit to determine the local photopeak count.

30. The system of claim 29 wherein the quasi-local pixels comprise large pixels made up of $(2n+1) \times (2m+1)$ rectangles of pixels where both n and m are positive integers.
means for dividing the value of the large pixel by the number of pixels in the large pixel,
means for attributing the quotient as the pixel value to the center pixel, and
means for evaluating all pixels in this manner.

31. The system of claim 24 wherein the means for fitting the trial function to the measured energy spectrum comprises means for a least square fitting.

32. The system of claim 24 wherein the means for fitting the trial function to the measured energy spectrum comprises means for maximum likelihood fitting.

33. The system of claim 24 wherein the means for fitting the trial function to the measured energy spectrum comprises means for combining said least square fitting and said maximum likelihood fitting.

34. A system of producing practically Compton free images of a patient with a gamma ray imaging system, said system comprising:
means for determining a trial function, said means for determining a trial function comprising:
means for multiplying a known system energy spread function by an unknown count number due to unscattered photons,
means for convolving at least a first order distribution of the scattered photons derived from the probability of physical interaction of the photons and the known system energy spread function to provide a system dependent Compton energy distribution,
means for multiplying the system dependent Compton energy distribution by an unknown number corresponding to counts of scattered photons,
means for measuring an energy spectrum of the patient that includes total counts due to scattered and to unscattered photons,
means for fitting the trial function to the measured energy spectrum to determine the unknown count number due to unscattered photons, and
means for using the count number due to the unscattered photons to produce the practically Compton free images.

35. The system of claim 34 including means for determining the unknown count number due to the unscattered photons within seconds of finishing measuring an energy spectrum.

36. The system of claim 34 wherein means for determining the trial energy function includes converting Nishina-Klein's equation to a first order photon scatter probability energy distribution. and
means for using the converted Nishina-Klein equation to obtain the energy distribution of first order scattered photons.

37. The system of claim 36 including means for convolving the energy distributions of first order scattered photons to obtain energy distributions of higher orders of scattered photons.

38. The system of claim 37 including means for integrating the Compton energy distribution for each of the matrices to obtain a set of discrete functions.

39. The system of claim 38 wherein the means for measuring the energy function includes:
means for determining an X,Y location and an energy of photons impinging on a system photon detector.
means for determining the energy of the detected photons,
a plurality of matrices having X,Y pixels corresponding to the impinging locations to accumulate counts of impinging photons, each of said matrices corresponding to an energy window, said plurality of matrices extending over an energy range, and
means for constructing the measured energy spectrum from the accumulated counts in the matrices.

40. The system of claim 39 including means for orthonormalizing the discrete functions.

41. The system of claim 40 including means for using a Graham-Schmitt procedure for the orthonormalization.

42. The system of claim 34 wherein the means for fitting the trial function to the measured energy spectrum includes means for a least square fitting.

43. The system of claim 34 wherein the means for fitting the trial function to the measured energy spectrum includes means for maximum likelihood fitting.

44. The system of claim 34 wherein the means for fitting includes a combination of said least square fitting and said maximum likelihood fitting.

* * * * *